United States Patent
Pichette et al.

(10) Patent No.: US 9,532,962 B2
(45) Date of Patent: Jan. 3, 2017

(54) MEDIUM-CHAIN LENGTH FATTY ACIDS AND GLYCERIDES AS NEPHROPROTECTION AGENTS

(75) Inventors: Vincent Pichette, St. Hyacinthe (CA); Francois Leblond, Le Gardeur (CA); Mouna Lagraoui, Laval (CA); Lyne Gagnon, Laval (CA)

(73) Assignee: PROMETIC PHARMA SMT LIMITED, Cambridge (GB)

( * ) Notice: Subject to any disclaimer, the term of this patent is extended or adjusted under 35 U.S.C. 154(b) by 1103 days.

(21) Appl. No.: 12/740,700

(22) PCT Filed: Nov. 3, 2008

(86) PCT No.: PCT/CA2008/001930
§ 371 (c)(1),
(2), (4) Date: Jul. 27, 2010

(87) PCT Pub. No.: WO2009/055933
PCT Pub. Date: May 7, 2009

(65) Prior Publication Data
US 2010/0286269 A1    Nov. 11, 2010

Related U.S. Application Data

(60) Provisional application No. 60/985,094, filed on Nov. 2, 2007.

(51) Int. Cl.
*A61K 31/20* (2006.01)
*A61K 31/23* (2006.01)
*A61K 45/06* (2006.01)

(52) U.S. Cl.
CPC .............. *A61K 31/20* (2013.01); *A61K 31/23* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 7,745,488 B2 * | 6/2010 | Gagnon et al. | 514/517 |
| 2004/0052836 A1 | 3/2004 | Li et al. | |
| 2004/0147599 A1 * | 7/2004 | Gagnon | A61K 31/18 514/517 |

FOREIGN PATENT DOCUMENTS

| EP | 0 583 480 A1 | 2/1994 |
|---|---|---|
| WO | WO 02/083120 A2 | 10/2002 |
| WO | WO 02/083122 A1 | 10/2002 |
| WO | WO 03/001982 A2 | 1/2003 |
| WO | WO 2004/069237 A1 | 8/2004 |
| WO | WO 2005/012217 A2 | 2/2005 |
| WO | WO 2007/117272 A2 | 10/2007 |

OTHER PUBLICATIONS

Nazneen et al. "Possible Role of Ets-1 and MMP-1 in Matrix Remodeling in Experimental Cisplatin Nephropathy". Med Electron Microsc. 2002; 35:242-247.*
Alberts et al. "Cisplatin-Associated Neurotoxicity: Can It Be Prevented?". Anticancer Drugs. Jun. 1995; 6(3):369-383. [Abstract Only].*
Tortora et al. "Appendix C: Normal Values for Selected Blood Tests". Principles of Anatomy and Physiology (Tenth Edition). John Wiley and Sons, Inc. 2003. pp. C-O to C-2.*
Ng et al. "Tubular Epithelial-Myofibroblast Transdifferentiation in Progressive Tubulointerstitial Fibrosis in 5/6 Nephrectomized Rats". Kidney International, 1998; 54:864-876.*
International Preliminary Report on Patentability from International Application No. PCT/CA2008/001930, dated May 4, 2010 (date of issuance of report) and May 14, 2010 (date of mailing of report).
International Search Report from International Application No. PCT/CA2008/001930, dated Jan. 6, 2009 (date of completion of search) and Feb. 5, 2009 (date of mailing of report).
Hong et al., "Effect of Glucuronidation Substrates/Inhibitors on $N$-(3,5-Dichlorophenyl) Succinimide Nephrotoxicity in Fischer 344 Rats," Toxicology 132:43-55, 1999.
Hurd et al., "Prevention of Glomerulonephritis and Prolonged Survival in New Zealand Black/New Zealand White $F_1$ Hybrid Mice Fed an Essential Fatty Acid-Deficient Diet," J. Clin. Invest. 67:476-485, 1981.
Monserrat et al., "Protective Effect of Myristic Acid on Renal Necrosis Occurring in Rats Fed a Methyl-Deficient Diet," Res. Exp. Med. 199:195-206, 2000.
Extended European Search Report from European Patent Application No. 08845122.4, dated Dec. 22, 2010.

(Continued)

*Primary Examiner* — Leslie A. Royds Draper
(74) *Attorney, Agent, or Firm* — Clark & Elbing LLP; Susan M. Michaud (57) ABSTRACT

Use of medium-chain length fatty acids such as capric acid, caprylic acid or lauric acid and their salts or mono- or di- or triglycerides as nephroprotection agents to protect against renal failure progression in chronic kidney diseases This includes the treatment of kidney diseases associated with nephrectomy, renal fibrosis, glomerular sclerosis and end-stage renal disease Also includes the protection of the kidney against cytotoxic agent used in chemotherapy or autoimmune diseases or transplantation Further includes the treatment of renal failure progression associated with hypertension, infarct, tumor, diabetes mellitus, autoimmunity or inflammation.

13 Claims, 8 Drawing Sheets

(56) References Cited

OTHER PUBLICATIONS

"Cisplatin (Cisplatin Injection) Drug Information: Side Effects and Drug Interactions," RxList, Inc., Dec. 17, 2013 (5 pages).
Keskin et al., "Biweekly triplet chemotherapy with gemcitabine, cisplatin and vinorelbine for advanced chemotherapy naïve non-small cell lung cancer," Tumori. 99(4):463-8 (2013). Abstract provided.
Yao et al., "Cisplatin Nephrotoxicity: A Review," Am J Med Sci. 334(2):115-24 (2007).

* cited by examiner

MEDIUM-CHAIN LENGTH FATTY ACIDS AND GLYCERIDES AS NEPHROPROTECTION AGENTS

CROSS-REFERENCE TO RELATED APPLICATIONS

This application is the U.S. national stage filing under 35 U.S.C. §371 of international application PCT/CA2008/001930, filed Nov. 3, 2008, which claims benefit of provisional Application No. 60/985,094, filed Nov. 2, 2007.

FIELD OF THE INVENTION

The present invention relates to protection against renal failure progression in chronic kidney diseases. This includes the treatment of kidney diseases associated with nephrectomy, renal fibrosis, glomerular sclerosis, and end-stage renal disease. This also includes protection of the kidney against cytotoxic agents used in chemotherapy or autoimmune diseases or transplantation. This further includes the treatment of renal failure progression associated with hypertension, infarct, tumor, diabetes mellitus, autoimmunity, or inflammation. The present invention also relates to reducing drug toxicity (e.g., antibiotic, analgesic) to the kidney. In particular, the present invention relates to the use of medium-chain length fatty acids such as capric acid, caprylic acid, or salts or triglycerides thereof or mono- or diglycerides or other analogues thereof as a nephroprotective agent.

BACKGROUND OF THE INVENTION

The kidney is a structurally complex organ that has evolved to perform a number of important functions: e.g., excretion of the waste products of metabolism, regulation of body water and salt, maintenance of appropriate acid balance, and secretion of a variety of hormones and autocoids. Diseases of the kidney are as complex as its structure, but their study is facilitated by dividing them into those that affect four basic morphologic components: i.e., glomeruli, tubules, interstitium, and blood vessels. This traditional approach is useful because the early manifestations of diseases that affect each of these components tend to be distinctive. Further, some components appear to be more vulnerable to specific forms of renal injury. For example, glomerular diseases are often immunologically mediated, whereas tubular and interstitial disorders are more likely to be caused by toxic or infectious agents. Nevertheless, some disorders affect more than one structure. In addition, the anatomic interdependence of structures in the kidney implies that damage to one almost always secondarily affects the others. Thus, severe glomerular damage impairs flow through the peritubular vascular system; conversely, tubular destruction, by increasing intraglomerular pressure, may induce glomerular atrophy. Thus, whatever the origin, there is a tendency for all forms of chronic renal disease ultimately to destroy all four components of the kidney, culminating in chronic renal failure and what has been called end-stage contracted kidneys (Cotran et al., Basic Pathology, Sixth Edition, 1997).

Chemotherapy and immunosuppressive therapy refers to the use of cytotoxic or immunosuppressive agents such as, but not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin, or chlorambucil, and cyclosporin A, tacrolimus, rapamycin, or corticosteroids to treat cancer patients or to inhibit graft rejection in transplant patients. Despite their efficacies, these agents are non-specific and, particularly at high doses, they are toxic to normal and rapidly dividing cells. Furthermore, their use may be limited by inherent untoward effects, of which acute myelosuppression, nephrotoxicity, cardiotoxicity, neurotoxicity, gastrointestinal, bladder, and pulmonary toxicities may worsen patient outcome over long time periods.

In autoimmune diseases such as diabetes mellitus, the kidneys are prime targets to suffer tissue damage or lesions. Three important lesions are encountered: (1) glomerular lesions; (2) renal vascular lesions, principally arteriolosclerosis; and (3) pyelonephritis, including necrotizing papillitis. Nephrectomy, or kidney removal, can also lead to renal dysfunction. Nephrectomy is performed on patients with cancer of the kidney (i.e., renal cell carcinoma); polycystic kidney disease in which sac-like structures displace healthy tissue; and serious infection of the kidney. It is also used to remove a healthy kidney from a donor for the purpose of kidney transplantation. Because the kidney is responsible for filtering wastes and fluid from the bloodstream, kidney function is critical to life. Nephrectomy candidates suffering from serious kidney disease, cancer, or infection usually have few treatment choices but to undergo the procedure. But if function is lost in the remaining kidney, the patient will require chronic dialysis treatments or transplantation of a healthy kidney to sustain life. Therefore, there exists a need for drugs with a good safety profile which can be administered to patients with kidney disease which can prolong kidney health or protect it from deterioration to the extent that the kidney can no longer function.

SUMMARY OF THE INVENTION

The present invention satisfies the need for nephroprotective agents by providing a novel method for the protection of the kidney in a mammal, including a human patient, in need of such treatment. The present invention also provides a novel method for treating the nephrotoxic effects of chemotherapy, immunosuppressive, and corticosteroids therapies and any other situation in which the protection of the kidney can be of therapeutic value.

In accordance with this method, a composition comprising an effective amount of one or more compounds such as capric acid, caprylic acid, lauric acid or metallic salts (e.g., sodium, potassium, calcium, magnesium) or triglycerides thereof or mono- or diglycerides thereof in a pharmaceutically acceptable carrier is administered to a mammal, particularly a human, to significantly increase the protection of the kidneys or sole healthy kidney.

Accordingly, it is an object of the present invention to provide compositions using an effective amount of one or more compounds such as capric acid, caprylic acid, lauric acid or metallic salts (sodium, potassium, calcium, magnesium) or triglycerides thereof, or mono- or diglycerides thereof for the production of chemoprotective or immunosuppressive or anti-inflammatory or antibiotic or analgesic pharmaceutical compositions as a single agent or as a combination of two or more agents with and/or without drugs which induce nephrotoxicity.

Another object of the present invention relates to the use of capric acid, caprylic acid, lauric acid or sodium salts or triglycerides thereof or mono- or diglycerides thereof as an agent for the prevention or protection of drug-induced toxicity such as but not limited to cardiotoxicity, neurotoxicity, gastrointestinal, bladder, and pulmonary toxicities.

It is an object of the present invention to provide a protective or preventive method effective for providing chemoprotection of a mammal, including a human patient.

Another object of the present invention is to provide a method effective for increasing the efficacy of chemotherapy and radiation therapy in a mammal, including a human patient.

Yet another object of the invention is to provide methods for using more usual doses or even increasing the dose of chemotherapeutic compositions necessary to achieve a better therapeutic benefit, while avoiding increased side effects such as but not limited to nephrotoxicity, cardiotoxicity, and neurotoxicity.

Finally, another object of the present invention is to provide a method that causes minimal or no adverse effects to the recipient. The mammal, including a human patient, may be selected as in need of treatment prior to such treatment.

These and other objects, features and advantages of the present invention will become apparent after a review of the following detailed description of the disclosed embodiment and the appended claims.

DETAILED DESCRIPTION OF SPECIFIC EMBODIMENTS

Renal kidney disease associated with one or more of nephrectomy, renal fibrosis, glomerular sclerosis, and end-stage renal disease are observed in hypertension, infarct, tumor, diabetes mellitus, and autoimmune or inflammatory diseases. Cytotoxic drugs used in chemotherapy, immunosuppressive or anti-inflammatory (e.g., steroidal and non-steroidal) drugs used in transplantation or autoimmune diseases, antibiotic, or analgesic drugs also induce nephrotoxicity. Subsequently, the patient can be severely affected.

The present invention relates to a method of protecting the renal system and can be extended to the cardiac and nervous systems. A patient with a chronic disease can show injury of many organs for example; a patient with statine diabetes mellitus needs nephroprotective measures against the renal lesion, cardioprotective measures for the cardiac lesion, and neuroprotective measures for any lesion of the nervous system. Current methods employed or treatments consist of organ-protective therapy, as well as protective measures that are aimed at correcting multiple organ dysfunctions concomitantly. Organ-protective measures focus on a single organ, such as nephroprotective, cardioprotective, or neuroprotective measures. Some organ-protective measures exhibit protective actions on other organs too. ACE inhibitors, for example, have a renal protective action, but at the same time they also have cardiac and cerebral protective actions. In this case, organ-protective measures cross into the field of multiple organ or multi-organ protection. The issue is to establish the common features of the kidney, the brain, and the heart to explain the similar lesions that impose common therapeutic protective measures. For example, hypertension concomitantly affects kidney, heart, and brain. The use of ACE inhibitors and angiotensin II receptor blockers will have complex nephro-, cardio-, and neuroprotective effects. Lesions secondary to artherosclerosis, as well as inflammatory diseases, will have an effect on the vascular endothelium. The use of statins will influence the lipid (mainly cholesterol) profile and consequently the effect of the latter on coronary, renal, and cerebral blood flow. Likewise, sulodexide exerts a protective effect on the vascular endothelium by correcting glycosaminoglycans. Glucose metabolism changes will also influence lipid metabolism. Low protein intake will also influence the protection of the kidney (J. Vet. Med. Sci. 69: 247-253, 2007). Inhibitors of cyclooxygenase-2 are also associated with modest nephroprotection in uninephrectomized diabetic rats; these effects are independent of metabolic control and blood pressure (Clin. Exp. Pharmacol. Physiol. 34: 36-41, 2007). Antagonists of endothelin A receptors seems also to affect progressive renal dysfunction (Hypertension 31: 995-1001, 1998) by decreasing expression of growth factors and collagen, and improving metalloprotieinase-2 activity in the kidneys (J. Cardiovasc. Pharmacol. 39: 892-900, 2002). Prophylactic administration of theophylline as an intravenous loading dose and oral maintenance regimen may preserve kidney function in terms of glomerular filtration rate in patients with cisplatin therapy (J. Am. Soc. Nephrol. 16: 452-458, 2005). Soy isoflavones, such as genistein, are antagonists of TGF-13 signaling in mesangial cells which may have nephroprotective potential (Medical Hypothesis 66: 1093-1114, 2006). Gamma-aminobutyric acid (GABA) also attenuates renal dysfunction via regulation of blood pressure and lipid profile, and it also ameliorates the oxidative stress induced by nephrectomy (J. Pharm. Pharmacol. 58: 1515-1525, 2006).

Hypoxia secondary to anemia that accompanies advanced chronic kidney disease concomitantly afflicts the heart and brain. Correction of anemia of chronic kidney disease through nephroprotective measures which consist of iron, folic acid, and erythropoietin will have consequences on the kidney by improving the reduced production of erythropoietin and its function. But they will also impact the heart by improving cardiac disease accompanied by renal and cerebral impairment. There are also limitations such as availability, toxicity, and efficacy which restrict the use of erythropoietin. However the ultimate need to halt disease progression in the long term is still pending. Because of the pathogenetic complexity of kidney disease, multidrug intervention with the least side effects should, without doubt, be the next step to stop kidney disease progression.

Medium-chain triglyceride(s) (MCT) can be made by esterifying glycerol with fatty acids having carbon chain lengths of 8 (C8, octanoic acid or caprylic acid) or 10 (C10, decanoic acid or capric acid). MCT is usually a mixture of glycerol esters of C8 and C10 fatty acids; however, MCT can also contain small amounts (2±1% each) of glycerol esters of C6 (hexanoic acid or caproic acid) and C12 (dodecanoic acid or lauric acid). Long-chain triglyceride(s) (LCT), on the other hand, consist of glycerol esterified with fatty acids with carbon chain lengths of greater than 12. Typical fatty acids present in LCT include palmitic (C16) and stearic (C18) acids. Unlike MCT, LCT is the primary component of dietary fats. Indeed, MCT and LCT have significantly different biological properties. Some of the physiological differences between MCT and LCT are described in *Harrison's Principles of Internal Medicine*, $8^{th}$ Edition, 1520-1521 (1977); $15^{th}$ Edition, 1668-1669 (2001). For example, MCT, in contrast to LCT, do not require hydrolysis by pancreatic lipase, since they can be absorbed by intestinal epithelial cells.

MCT and their constituent medium-chain fatty acids are nontoxic materials which are used in the food and pharmaceutical industries. For example, Traul et al. (Food Chem. Toxicol. 38:79-98, 2000) state that MCT have been utilized in an increasing number of food and nutrition applications because they offer a number of advantages over LCT. MCT are also used primarily as emulsifiers in various human and veterinary pharmaceutical preparations and in cosmetics. They refer to a number of toxicological studies which support the safety of MCT. For example, they note that the safety of human dietary consumption of MCT, up to levels of 1 g/kg, has been confirmed in clinical trials. C8 and C10 fatty acids possess similar safety and use. For example, in *The Merck Index*, $11^{th}$ Edition, 266 (1989) caprylic acid is reported to have an $LD_{50}$ (oral, rats)=10.08 g/kg which is essentially nontoxic. In fact, according to part 184 of the Code of Federal Regulations (CFR), the U.S. Food and Drug Administration (FDA) has granted caprylic acid a GRAS (Generally Recognized As Safe) affirmation. Similarly, according to part 172 (CFR) free fatty acids (e.g., capric, caprylic) and their metallic salts are recognized as safe additives for use in food. As noted by Dimitrijevic et al. (J. Pharm. Pharmacol. 53:149-154, 2001), capric acid (sodium salt) is approved for human use in Japan and Sweden as an absorption enhancer for rectal drug products. U.S. Pat. No. 4,602,040 (1986) describes the use of MCT as a pharmaceutical excipient. More recently, WO 01/97799 describes the use of medium-chain fatty acids, in particular caprylic and capric acids, as antimicrobial agents.

Until the unexpected findings disclosed herein, however, the effectiveness of medium-chain fatty acids such as capric acid, caprylic acid or metallic salts or mono-, di- or triglycerides (MCT) thereof for nephroprotection was unknown. As described herein, MCT may comprise triglycerides of C8 (caprylic), C10 (capric) and C12 (lauric) fatty acids which constitute the activity pertaining to the nephroprotection. Indeed, this discovery was completely unexpected since very little has been reported in the literature with regard to the controversial effect of unsaturated long chain fatty acids or triglycerides on nephroprotection. Furthermore, influences of essential fatty acids and triglycerides as reasons for the progression of chronic renal failure are still in debate. The efficiency of fatty acid or diet in the treatment of chronic renal disease is controversial. The outcome of four diets containing different concentrations of triglycerides and essential fatty acids in 5/6 nephrectomized rats showed no significant differences in survival rate, proteinuria, urea and creatinine levels as well as histological findings in the different groups (Nephron 38: 233-237, 1984). The composition of dietary polyunsaturated fatty acids (PUFA) modifies the course of induced renal disease in rats (Prostaglandins 32: 211-219, 1986; J. Am. Soc. Nepthrol.

1: 1343-1353, 1991; Metabolism 41: 382-389, 1992; Kidney Intl. 32: 700-709, 1987). In some laboratory studies (Prostaglandins 32: 211-219, 1986; J. Am. Soc. Nepthrol. 1: 1343-1353, 1991), dietary supplementation with (n=3) PUFA was nephroprotective; however, in others (Metabolism 41: 382-389, 1992; Kidney Intl. 32: 700-709, 1987), PUFA supplementation was associated with worsening glomerulosclerosis and/or decrements in glomerular filtration rate. Results of studies in human beings are similarly conflictive, with benefits (N. Engl. J. Med. 331: 1194-1199, 1994) or no effect reported (Kidney Intl. 44: 75-86, 1993). In summary, the prior art does not teach that medium-chain fatty acids or triglycerides or metallic salts possess nephroprotective activity.

The present invention relates to the use of medium-chain fatty acids or metallic salts or triglycerides thereof or mono- or diglycerides thereof as a nephroprotective agent. Depending on the medical needs, medium-chain fatty acids or metallic salts or triglycerides thereof or mono- or diglycerides thereof is administered before, during and/or after the treatment in order to protect the kidney or other organs or to delay renal dysfunction. Furthermore, it is possible to use a combination of medium-chain fatty acids along with their metallic salts or triglycerides thereof or mono- or diglycerides thereof at multiple points relative to treatment with other nephroprotective agents. Alternatively, it is possible to administer the compounds for nephroprotection before, during and/or after treatment with chemotherapy, radiotherapy, immunosuppressive drugs, antibiotics, analgesics, and pathologies associated with kidney diseases.

A "therapeutically effective amount" of the compound(s) is used. Such an effective amount may be determined by varying its dose to achieve the desired therapeutic affect(s) such as, for example, providing nephroprotection, suppressing deleterious effects on kidney morphology, reducing the number and/or severity of symptoms of kidney disease, or any combination thereof. One or more compounds as the active pharmaceutical ingredient(s) can be formulated in a pharmaceutical composition with a pharmaceutically acceptable carrier.

As used herein, the term "pharmaceutically acceptable carrier" refers to a substance that does not interfere with the physiological effects of medium-chain fatty acids such as capric acid or caprylic acid or lauric acid or metallic salts or triglycerides thereof or mono- or diglycerides thereof and that is not toxic to mammals including humans.

A pharmaceutical composition may be formulated using capric or caprylic or lauric acid or salts or triglycerides thereof or mono- or diglycerides thereof or MCT and pharmaceutically acceptable carriers by methods known to those skilled in the art (*Merck Index*, Merck & Co., Rahway, N.J.). These compositions include, but are not limited to, solids, liquids, oils, emulsions, gels, aerosols, inhalants, capsules, pills, patches and suppositories.

Methods to produce a pharmaceutical composition include bringing together one or more active ingredients into association with a pharmaceutically acceptable carrier which constitutes one or more accessory ingredients.

As used herein, the term "nephroprotection" refers to a process by which the rate of disease progression in the kidney is delayed or stopped and so the kidney is subsequently protected.

When the method of this invention is applied to drug-induced nephrotoxicity, capric or caprylic or lauric acid or salts or triglycerides thereof or mono- or diglycerides thereof can be administered prior to, during, or subsequent to the drug (i.e., prior to, during, or subsequent to the administration of a cytotoxic agent or anti-inflammatory or immunosuppressive drugs).

By "cytotoxic agent" is meant an agent which kills highly proliferating cells: e.g., tumors cells, virally infected cells, or hematopoietic cells. Examples of a cytotoxic agent which can be used to practice the invention include, but are not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin or chlorambucil, and an agonist of any of the above compounds. A cytotoxic agent can also be an antiviral agent: e.g., AZT (i.e. 3'-azido-3'-deoxythymidine) or 3TC/lamivudine (i.e. 3-thiacytidine).

Nephroprotection refers to protection provided to a mammal from the toxic effects arising from treatment of the mammal with a chemotherapeutic agent. Most often, the latter is a cytotoxic agent whose therapeutic effect arises from its ability to interfere with or inhibit some aspect of DNA replication, RNA transcription, or subsequent translation of protein. Therefore, a nephroprotective agent refers to any compound administered to a mammal which would protect the mammal, or facilitate the recovery of the animal, from the toxic effects resulting from treatment of the mammal with a chemotherapeutic agent.

Renal dysfunction associated with drugs or pathologies (e.g. autoimmune disease) can be diagnosed and its severity can be determined by a person skilled in the art. The term "renal dysfunction" may refer to that condition which exists when several parameters are observed such as but not limited to proteinurea, serum urea nitrogen, creatinine, creatinine clearance, uremia, glomerular filtration rate, and tubulointerstitial fibrosis. Without limitation, renal dysfunction may result in renal failure and death. Efficacy of treatment can also be determined by a person skilled in the art. It may also provide a palliative effect.

In one preferred embodiment of this invention, the pharmaceutical composition is in the form of any suitable composition for oral, sublingual, rectal, topical administration or inhalation (e.g., nasal spray), intramuscular, intradermal, intraperitoneal, subcutaneous, or intravenous administration for use in nephroprotection or the treatment of renal disease.

It will be appreciated that the amount of a compound required for use in the treatment will vary with the route of administration, the nature of the condition being treated, the age and condition of the patient, and will ultimately be at the discretion of the attending physician. The desired dose may be conveniently presented in a single dose or as divided doses taken at appropriate intervals, for example as two, three or more doses per day as necessary to effect or bring about treatment. The term "treatment" or "treating" includes any therapy of existing disease or condition and prophylaxis of the disease or condition (e.g., renal diseases) in a mammal. This includes (a) preventing the disease or condition from occurring in a patient which may be predisposed to the disease but has not yet been diagnosed as having it, (b) inhibiting or arresting the development of the disease or condition and (c) relieving the disease or condition by causing its regression or the amelioration of one or more symptoms.

While it is possible that, for use in therapy, medium-chain fatty acids or metallic salts or triglycerides thereof or mono- or diglycerides thereof may be administered as the raw chemical, it is preferable to present the active pharmaceutical ingredient as a pharmaceutical formulation or composition. A nontoxic composition is formed by the incorporation of any of the normally employed excipients such as, for example but not limited to, mannitol, lactose, trehalose, starch, magnesium stearate, talcum, cellulose, carboxymethyl cellulose, glucose, gelatin, sucrose, glycerol, magnesium carbonate, sodium citrate, sodium acetate, sodium chloride, sodium phosphate, and glycine.

In another embodiment, the pharmaceutical composition is in a form suitable for enteral, mucosal (including sublingual, pulmonary and rectal) or parenteral (including intramuscular, intradermal, intraperitoneal, subcutaneous, and intravenous) administration. The formulations may, where appropriate, be conveniently presented in discrete dosage units and may be prepared by any of the methods well known in the art of pharmacy. All methods include the step of bringing into association the active pharmaceutical ingredient with liquid carriers or finely divided solid carriers or both and then, if necessary, shaping the product into the desired form. When desired, the above-described formulations adapted to give sustained release of the active pharmaceutical ingredient may be employed. Sustained release formulations well known to the art include the use of liposomes, biocompatible polymers, a bolus injection or a continuous infusion.

Medium-chain fatty acids or salts or triglycerides thereof or mono- or diglycerides thereof can also be used in combination with other therapeutically active agents such as cytotoxic anticancer or antibiotics or immune suppressive drugs (including anti-inflammatory drugs). The individual components of such combinations may be administered either sequentially or simultaneously in separate or combined pharmaceutical formulations. The combination referred to above may conveniently be presented for use in the form of a pharmaceutical formulation and thus pharmaceutical formulations comprising a combination defined above together with a pharmaceutically acceptable carrier thereof comprise a further aspect of the invention.

EXAMPLES

The following examples further illustrate the practice of this invention but are not intended to be limiting thereof.

Example 1

In Vivo Effect of Sodium Caprate on Kidney Protection in 5/6 Nephrectomized Rat Model Demonstration of the in vivo protection effect of sodium caprate was undertaken in the 5/6 nephrectomized (Nx) rat model using the following procedure. Male 6 week-old Wistar rats were subjected to 5/6 nephrectomy or sham operations. Under ketamine anesthesia (60 to 100 mg/kg, i.p.), renal ablation was achieved by removing two-thirds of the left kidney followed by a right unilateral nephrectomy 7 days later. Sham rats underwent exposition of the kidneys and removal of the perirenal fat. Twenty-one days after the first operation, rats were assigned in the study if the serum creatinine was greater than 125 μmol/L indicating a dysfunction of the kidney. Animals that underwent the sham operation were given vehicle (saline) and were used as controls. Nx animals were divided in groups receiving the vehicle or sodium caprate. Saline or sodium caprate was given by gastric gavage once daily for 35 days. Serum creatinine was measured weekly in order to assess the severity of this end-stage renal disease model. Rats were sacrificed at day 63.

Figure 1:
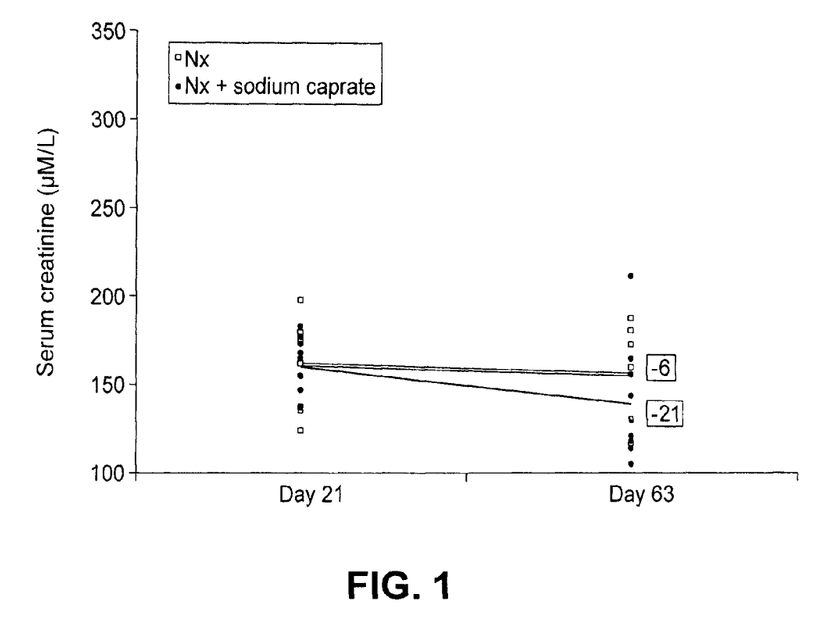
FIG. 1 shows the effect of sodium caprate on concentration of serum creatinine in nephrectomized (Nx) rats.

FIG. 1 represents the concentration of creatinine in serum in Nx and sodium caprate treated Nx rats. A weak diminution (6 μM/L) of serum creatinine was observed in saline-treated Nx rats. A stronger diminution (21 μM/L) of serum creatinine was observed in sodium caprate-treated Nx rats.

Figure 2:
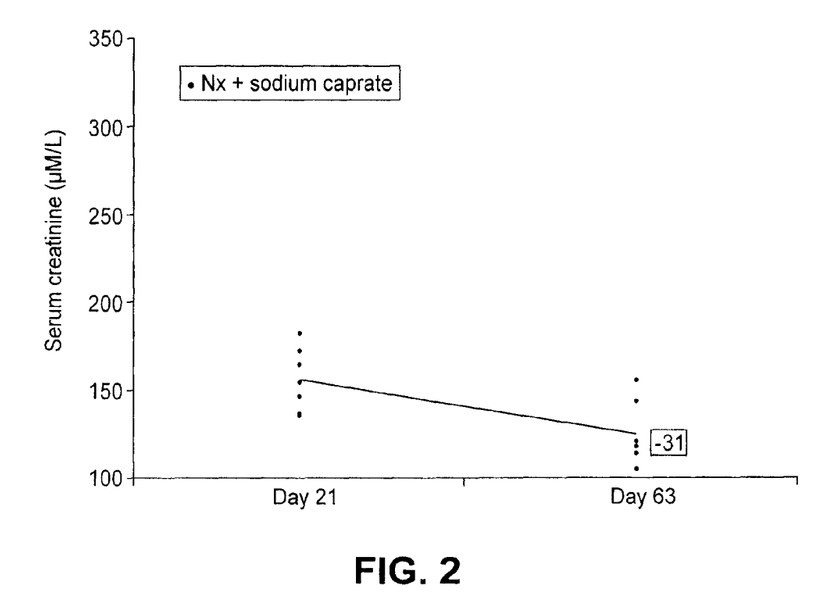
FIG. 2 shows the nephroprotective effect of sodium caprate on concentration of serum creatinine in sodium caprate-treated nephrectomized (Nx) rats.

From these Nx rats, 80% of the animals treated with sodium caprate demonstrated a mean of reduction of 31 μM/L of their initial serum creatinine concentration indicating a strong protection of the kidney compared to no protection observed in the saline-treated Nx rats (FIG. 2).

Figure 3:
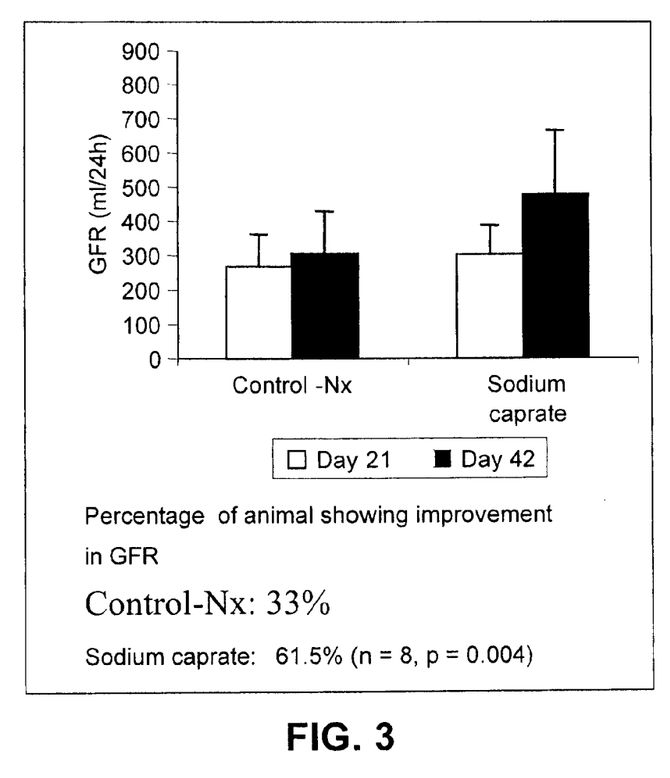
FIG. 3 shows the Nephroprotective effect of sodium caprate on GFR (creatinine clearance) in sodium caprate-treated nephrectomized (Nx) rats.

FIG. 3 illustrates that sodium caprate-treated Nx rats demonstrate a significant (p=0.004) increase in creatinine clearance (Glomerular Filtration Rate; GFR) compared to control-Nx rats from day 21 to day 42.

Figure 4:
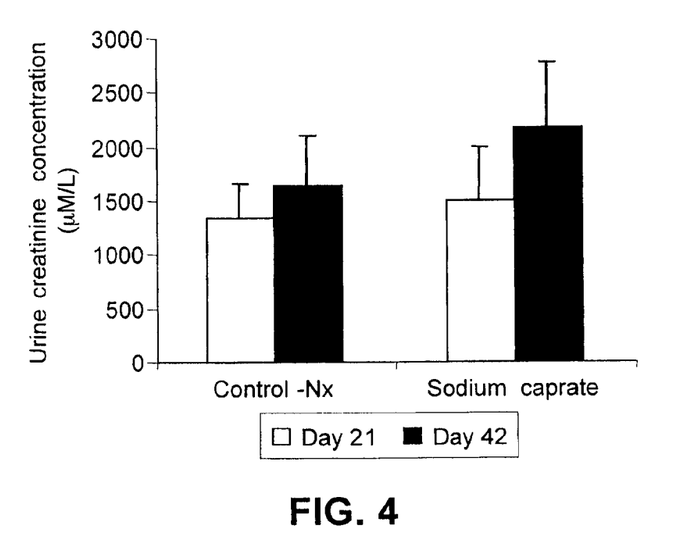
FIG. 4 shows the nephroprotective effect of sodium caprate on concentration of urine creatinine in sodium caprate-treated nephrectomized (Nx) rats. P value of urine creatinine concentration of day 42 compared to day 21: sodium caprate p=0.0002.
Figure 5:
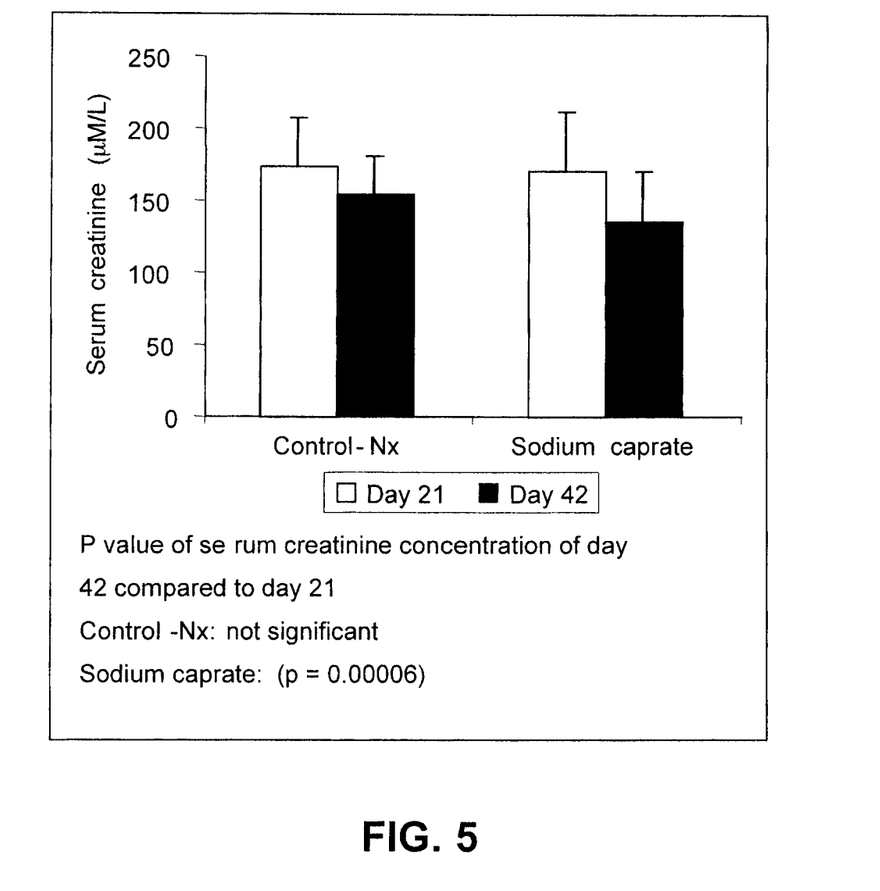
FIG. 5 shows the nephroprotective effect of sodium caprate on concentration of serum creatinine in sodium caprate-treated nephrectomized (Nx) rats.

Furthermore, a significant (p=0.0002) increase in urine creatinine was observed from day 21 to day 42 in sodium caprate-treated Nx rats (FIG. 4). This was reflected in a significant (p=0.00006) decrease in serum creatinine in sodium caprate-treated Nx rats compared to control Nx rats (FIG. 5).

Figure 6:
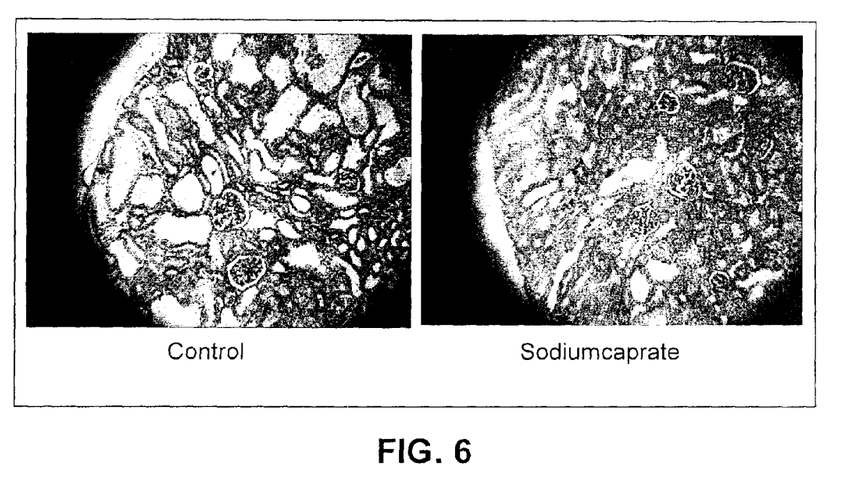
FIG. 6 shows histological micrographs (40×) of control and sodium caprate-treated nephrectomized rats.
Figure 7:
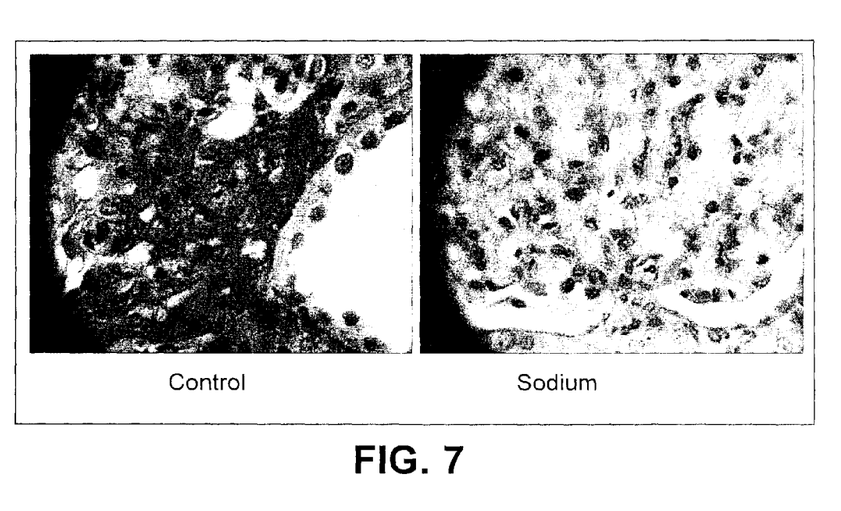
FIG. 7 shows histological micrographs (400×) of control and sodium caprate-treated nephrectomized rats.

FIGS. 6 and 7 represent the histological micrographs of control and sodium caprate-treated Nx rats. At 40× (FIG. 6), kidney structure (density, glomerulus and tubular structure) is more conserved in sodium caprate-treated Nx rats compared to control. In control Nx rats, sclerosis is well installed (FIG. 6) at the tubule level. Furthermore, at the glomerulus level (FIG. 7, 400×), fibrosis as shown by hyalin deposition is well implanted in the kidney of control Nx rats. In addition, necrosis of the mesangial tissue is observed. Treatment with sodium caprate reduces fibrosis and necrosis of the kidney tissue.

Example 2

Figure 8:
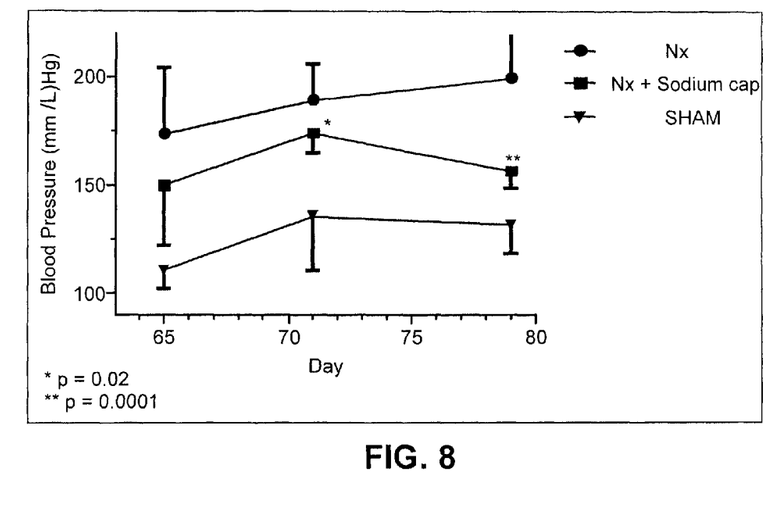
FIG. 8 shows the cardioprotective effect of sodium caprate on blood pressure in sodium caprate-treated nephrectomized (Nx) rats.

In Vivo Effect of Sodium Caprate on Heart Protection in 5/6 Nephrectomized Rat Model Demonstration of the heart protective effect of sodium caprate in vivo was undertaken in the 5/6 nephrectomized (Nx) rat model using the procedure described in example 1. Briefly, heart pressure was recorded with a RTBP 2000 (Kent Scientific) in 5/6 nephrectomized rats to demonstrate that sodium caprate exerts a protection of heart in severely affected 5/6 nephrectomized rats. A significant decrease in blood pressure was observed in sodium caprate-treated Nx rats (FIG. 8).

Example 3

In Vivo Effect of Sodium Caprate on Kidney Protection and Chemoprotection in Doxorubicin-Induced Nephrotoxicity Model Demonstration of the in vivo protection effect of oral administration of sodium caprate was undertaken in the doxorubicin-induced nephrotoxicity model using the following procedure. C57B1/6 mice (6-10 week-old) were treated with sodium caprate prophylacticly from day −3 to day 10 or treated therapeutically from day 1 to 10. Nephrotoxicity was induced by an intravenous injection of 10 mg/kg of doxorubicin at day 0, Serum creatinine and urea were monitored at day 4, 7 and 11.

Figure 9:
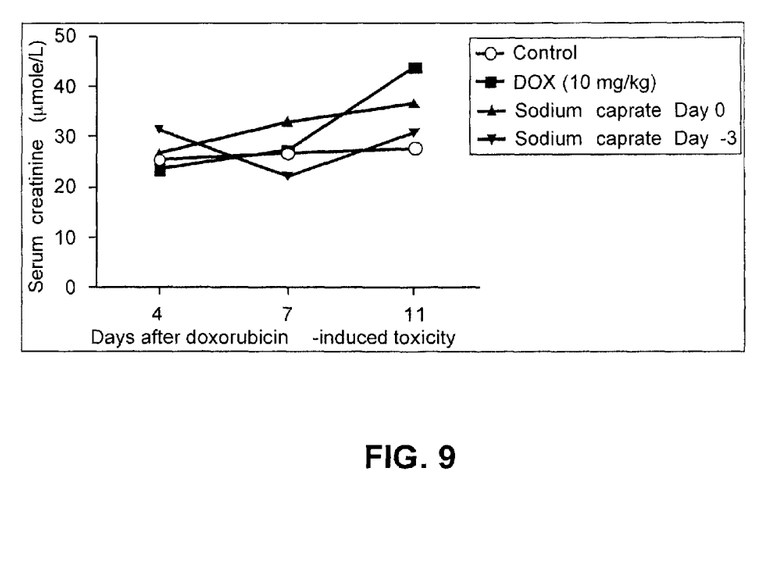
FIG. 9 shows the nephroprotective effect of sodium caprate on increased concentration of serum creatinine induced by doxorubicin (DOX) in mice.

Prophylactic treatment with sodium caprate inhibits the increase of serum creatinine induced by doxorubicin to a similar level observed in control mice (normal, no doxorubicin). Therapeutic treatment with sodium caprate reduces the serum creatinine level induced by doxorubicin (FIG. 9).

Figure 10:
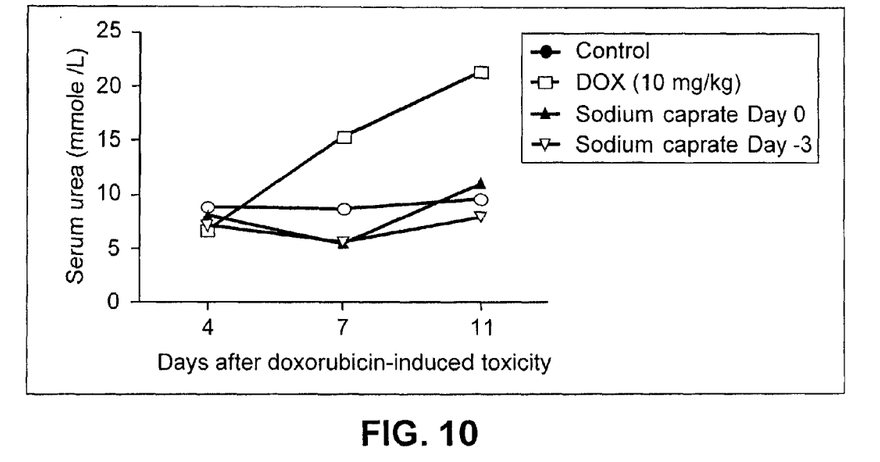
FIG. 10 shows the nephroprotective effect of sodium caprate on concentration of serum urea induced by doxorubicin (DOX) in mice.

Furthermore, prophylactic and therapeutic treatment with sodium caprate inhibits the increase of serum urea induced by doxorubicin to a similar level observed in control mice (normal, no doxorubicin; FIG. 10).

Figure 11:
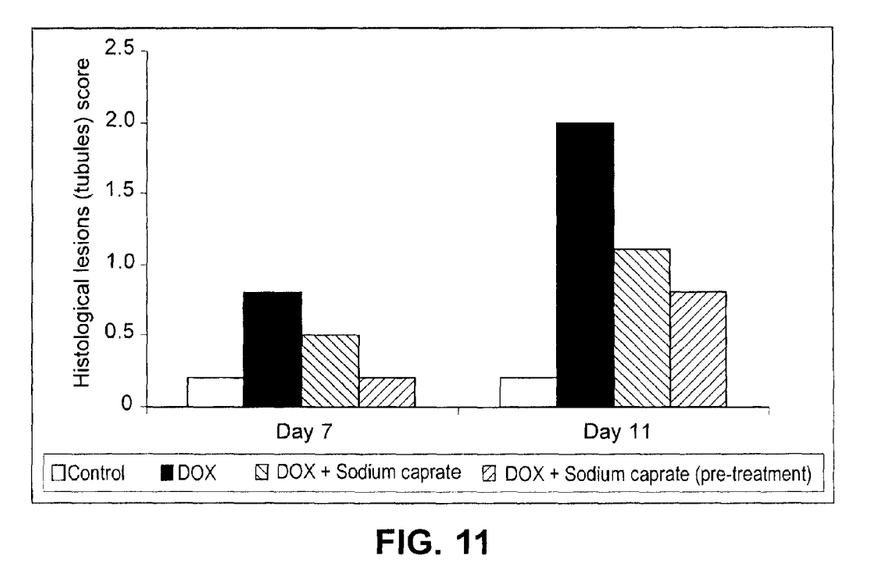
FIG. 11 shows the nephroprotective effect of sodium caprate on histological kidney (tubular) lesions induced by doxorubicin (DOX) in mice.

Doxorubicin is well known to induce nephro- and cardiotoxicity. FIG. 11 represents the histological kidney lesions score as determined by histochemistry in the doxorubicin-induced nephrotoxicity model. As shown in FIG. 11, doxorubicin induces significant kidney lesions at day 7 and 11. Prophylactic (pre-doxorubicin) and therapeutic (post-doxorubicin) treatments with sodium caprate reduce the kidney lesions at the tubular level induced by doxorubicin.

Figure 12:
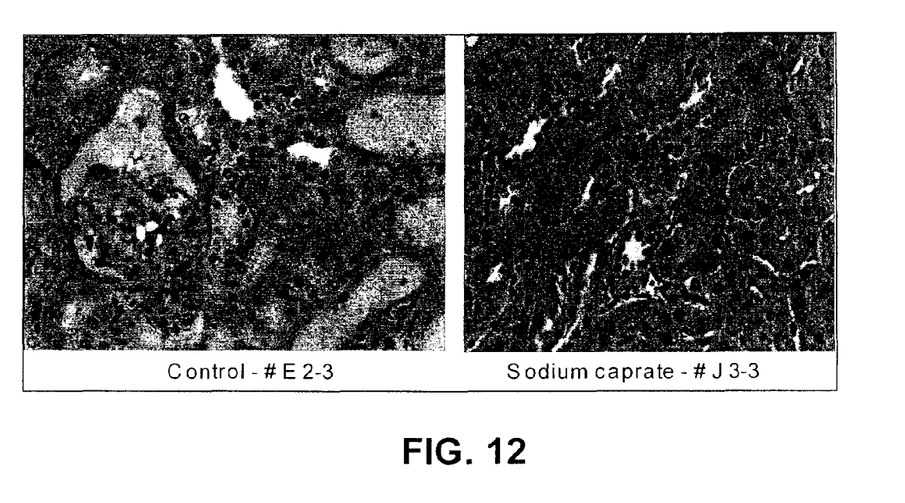
FIG. 12 shows histological micrographs (400×) of control and sodium caprate-treated mice in doxorubicin-induced nephrotoxicity model.

Doxorubicin induces early lesions primarily at the tubular region. Toxicity is further extended to the glomerulus (around day 11 post-doxorubicin). FIG. 12 represents the histological micrographs of doxorubicin-induced lesions in control and sodium caprate-treated (prophylactic treatment) mice. Doxorubicin induces kidney cell apoptosis, fibrosis, sclerosis, and accumulation of proteins in affected tubular regions. Prophylactic or therapeutic treatment with sodium caprate protects kidney against doxorubicin toxicity.

Example 4

In Vivo Effect of Tricaprin on Kidney Protection and Chemoprevention in Doxorubicin-Induced Nephrotoxicity Model Demonstration of the in vivo protection effect of oral administration of tricaprin was undertaken in the doxorubicin-induced nephrotoxicity model using the procedure described in example 3.

Figure 13:
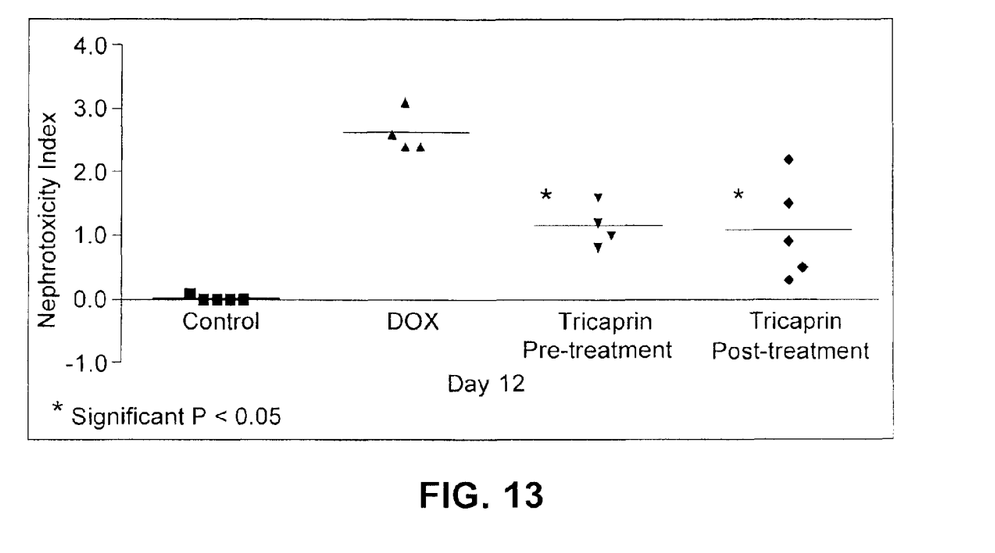
FIG. 13 shows the nephroprotective effect of tricaprin on histological kidney (tubular) lesions induced by doxorubicin (DOX) in mice.

FIG. 13 represents the histological kidney lesions score as determined by histochemistry in the doxorubicin-induced nephrotoxicity model. As shown in FIG. 13, doxorubicin induces significant kidney lesions at day 12. Prophylactic (pre-doxorubicin) and therapeutic (post-doxorubicin) treatments with tricaprin reduces the kidney lesions at the tubular level induced by doxorubicin.

Figure 14:
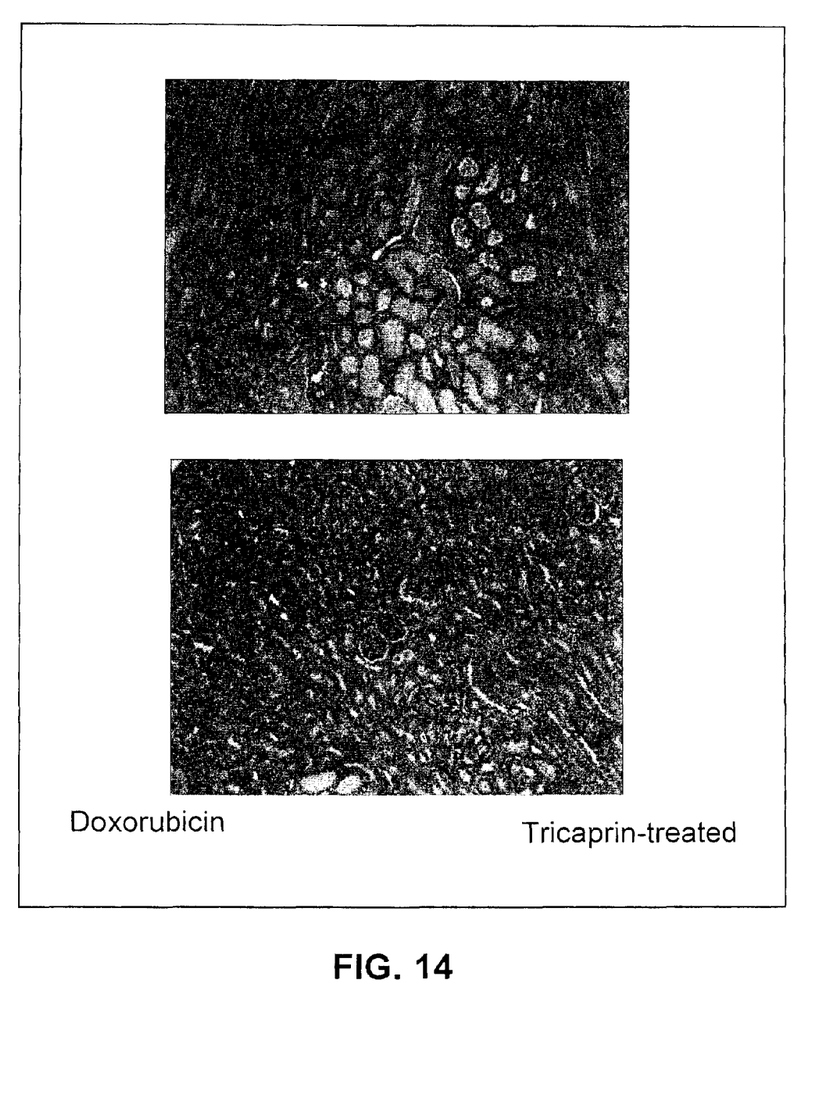
FIG. 14 shows histological micrographs (400×) of control and tricaprin-treated mice in doxorubicin-induced nephrotoxicity model.

FIG. 14 represents the histological micrographs of doxorubicin-induced lesions in control and tricaprin-treated (prophylactic treatment) mice. Doxorubicin induces kidney cell apoptosis, fibrosis, sclerosis and accumulation of proteins in affected tubular regions. Prophylactic or therapeutic treatments with tricaprin protects kidney against doxorubicin toxicity.

Patents, patent applications, and other publications cited herein are incorporated by reference in their entirety.

All modifications and substitutions that come within the meaning of the claims and the range of their legal equivalents are to be embraced within their scope. A claim using the transition "comprising" allows the inclusion of other elements to be within the scope of the claim; the invention is also described by such claims using the transitional phrase "consisting essentially of" (i.e., allowing the inclusion of other elements to be within the scope of the claim if they do not materially affect operation of the invention) and the transition "consisting" (i.e., allowing only the elements listed in the claim other than impurities or inconsequential activities which are ordinarily associated with the invention) instead of the "comprising" term. Any of the three transitions can be used to claim the invention.

It should be understood that an element described in this specification should not be construed as a limitation of the claimed invention unless it is explicitly recited in the claims. Thus, the claims are the basis for determining the scope of legal protection granted instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of the individual elements disclosed herein are considered to be aspects of the invention; similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A method of reducing or treating impaired kidney function resulting from renal fibrosis in a patient, the method comprising: identifying a patient in need of such reduction or treatment, and administering to said patient a composition comprising a therapeutically effective amount of at least one compound of formula I or at least one compound of formula II or combinations thereof:

Y = O, NH wherein
R1 is a straight chained or branched, saturated or unsaturated C7-C11 alkyl group;
A and B are independently hydrogen or and
X is a hydroxyl group, an oxy anion with a metallic mono- or dicationic counterion, or an alkoxy group with a straight chained or branched C1-C4 alkyl moiety.

2. The method according to claim 1, wherein said composition comprises a mixture of at least two compounds of formula I, and wherein said at least two compounds are medium chain triglycerides (MCT) where A equals B equals 3. The method according to claim 2, wherein said mixture consists of two MCT, a first MCT being of formula I where A and B each equal $CH_3(CH_2)_6CO$; and a second MCT being of formula I where A and B each equal $CH_3(CH_2)_8CO$.

4. The method according to claim 2, wherein said mixture consists of four geometric isomers of C8 and O10 fatty acid triglycerides of the structure:

| | 1 | 2 | 3 | 4 |
|---|---|---|---|---|
| n = | 6 | 6 | 6 | 8 |
| m = | 6 | 6 | 8 | 8 |
| p = | 6 | 8 | 8 | 8 |

5. The method according to claim 1, wherein said composition comprises at least one compound of formula II, and wherein said at least one compound of formula II is a medium-chain fatty acid where X is OH.

6. The method of claim 1, wherein said composition comprises at least one compound of formula II where X is an oxy anion with a metallic counterion selected from the group consisting of calcium, magnesium, potassium, and sodium.

7. The method according to claim 5, wherein said at least one compound is caprylic acid or capric acid or lauric acid.

8. The method according to claim 6, wherein said at least one compound is sodium caprylate or sodium caprate or sodium laurate.

9. The method according to claim 6, wherein said at least one compound is calcium caprylate or calcium caprate or calcium laurate.

10. The method according to claim 1, wherein said at least one compound is caprylic acid triglyceride or capric acid triglyceride or lauric acid triglyceride.

11. The method according to claim 1, wherein said composition reduces impaired kidney function resulting from renal fibrosis arising from: chemotherapy, radiotherapy, immunosuppressive drugs, anti-inflammatory drugs, and/or antibiotic drugs.

12. The method according to claim 1, wherein said composition reduces impaired kidney function resulting from renal fibrosis which arises from: an autoimmune disease, diabetes, hypertension, infarct, a tumor and/or an inflammatory disease.

13. The method according to claim 1, wherein said patient is further in need of cardioprotection due to impaired heart function and/or is further in need of neuroprotection due to impaired neurological function.

* * * * *